United States Patent
Moszner et al.

(10) Patent No.: US 6,653,375 B2
(45) Date of Patent: *Nov. 25, 2003

(54) URETHANE DI(METH)ACRYLATE DERIVATIVES OF 1,3-BIS(1-ISOCYANATO-1-METHYLETHYL)BENZENE

(75) Inventors: Norbert Moszner, Eschen (LI); Volker Rheinberger, Vaduz (LI); Thomas Völkel, Lindau (DE); Urs Karl Fischer, Arbon (CH)

(73) Assignee: Ivoclar AG (LI)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/236,787

(22) Filed: Jan. 25, 1999

(65) Prior Publication Data

US 2002/0082315 A1 Jun. 27, 2002

Related U.S. Application Data

(60) Provisional application No. 60/081,685, filed on Apr. 14, 1998.

(30) Foreign Application Priority Data

Jan. 28, 1998 (DE) ............................................ 198 03 979

(51) Int. Cl.[7] ............................... A61K 6/083; A61K 6/09

(52) U.S. Cl. ........................ 524/116; 524/115; 526/301

(58) Field of Search ................................ 523/115, 116; 526/301

(56) References Cited

U.S. PATENT DOCUMENTS

| | | | |
|---|---|---|---|
| 4,400,159 A | | 8/1983 | Orlowski et al. |
| 5,063,257 A | * | 11/1991 | Akahane et al. ............. 523/116 |
| 5,658,672 A | * | 8/1997 | Lenke et al. ................. 525/127 |

FOREIGN PATENT DOCUMENTS

| | | |
|---|---|---|
| DE | 2312559 | 9/1973 |
| DE | 691 19 254 T2 | 10/1996 |
| DE | 198 03 979.4 | 11/1998 |
| EP | 0 205 846 B1 | 12/1986 |
| EP | 0 441 383 A2 | 8/1991 |
| EP | 0 658 582 A1 | 6/1995 |
| EP | 0 441 383 B1 | 5/1996 |
| JP | 3-231908 | 10/1991 |
| JP | 3-239711 | 10/1991 |
| JP | 5-25240 | 2/1993 |

OTHER PUBLICATIONS

Fukushima et al., "Polyisocyanate–polythiol Compositions for Plastic Lenses," *Chemical Abstracts* 119:82 (1993).
Hourston, et al., "Polyurethane/Polystyrene One–Slot Interpenetrating Polymer Networks with Good Damping Ability: Transition Broadening Through Crosslinking, Internetwork Grafting and Compatibilization," *Polymers for Advanced Technologies*, 7:273–280 (1995).
Hourston et al., "Polyurethans/Polystyrene One–Shot Interpenetrating Polymer Networks with Good Damping Ability: (2/95). Transition Broadening Through Crosslinking, Internetwork Grafting and Compatibilization," *Polymers for Advanced Technologies* 7:273–280 (1996).
Peutzfeldt, "Resin Composites in Dentistry: The Monomer Systems," *Eur. J. Oral Sci.*, 105:97–116 (1997).

* cited by examiner

*Primary Examiner*—Peter Szekely
(74) *Attorney, Agent, or Firm*—Nixon Peabody LLP

(57) ABSTRACT

The invention relates to urethane di(meth)acrylate derivatives of 1-3-bis(1-isocyanato-1-methylethyl)benzene according to Formula (I)

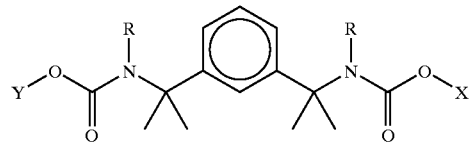

in which R is hydrogen or a straight-chained $C_1$–$C_8$ alkyl radical; X and Y independently of each other stand for

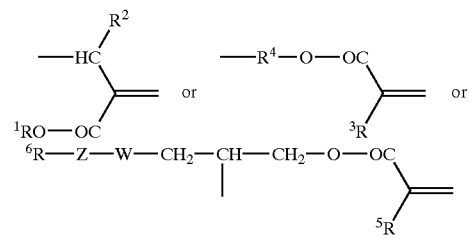

$R^1$ being a substituted or unsubstituted $C_6$- to $C_{12}$-aryl or $C_7$- to $C_{16}$-alkyl aryl radical; $R^2$ hydrogen, a $C_1$- to $C_5$-alkyl or a substituted or unsubstituted $C_6$- to $C_{12}$-aryl radical; $R^3$ hydrogen or a methyl radical; $R^4$ a $C_1$- to $C_8$-alkylene radical which can be broken by oxygen atoms, or a phenylene radical; $R^5$ hydrogen or a methyl radical; $R^6$ a substituted or unsubstituted $C_6$- to $C_{12}$-aryl or $C_7$- to $C_{16}$-alkyl aryl radical; Z being —CO— or a chemical bond and W standing for oxygen, sulphur or $NR^7$, $R^7$ being hydrogen or a straight-chained $C_1$- to $C_6$-alkyl radical. The substances are suitable in particular for the production of dental materials.

34 Claims, No Drawings

URETHANE DI(METH)ACRYLATE DERIVATIVES OF 1,3-BIS(1-ISOCYANATO-1-METHYLETHYL)BENZENE

This application claims priority benefit of U.S. Provisional Patent Application Ser. No. 60/081,685, filed on Apr. 14, 1998, which is hereby incorporated by reference.

The present invention relates to urethane di(meth) acrylate derivatives of 1,3-bis(1-isocyanato-1-methylethyl) benzene and to dental materials on the basis of these substances.

Urethane (meth)acrylates find practical applications inter alia as a constituent of adhesives, coatings and dental materials (R. Holman (Pub.), U.V. and EB. Curing Formulation for Printing Inks, Coatings and Paints, SITA-Technology, London 1984, 27; J. P. Foussier, J. F. Rabek (Pub.), Radiation Curing in Polymer Science and Technology, Vol. IV, Elsevier Applied Science, London and New York 1993, 387). A monomer which is used particularly frequently in the dental field is 7,7,9-trimethyl-4,13-dioxo-3,14-dioxa-5, 12-diazahexadecan-1,16-diyldimethacrylate (UDMA) which is accessible by reaction of one mole of 2,2,4-trimethylhexa-methylene diisocyanate with two moles of 2-hydroxyethyl methacrylate (HEMA) (cf. e.g. DE 195 44 671).

However, the refractive index of UDMA, at $n_D$=1.483, is clearly different from the refractive index of customary dental filling materials (ca. 1.52 to 1.55), so that UDMA and other aliphatic urethane dimethacrylates are frequently combined with bis-GMA, the addition product of methacrylic acid and bisphenol-A-diglycidyl ether (refractive index $n_D$=1.549) to match the refractive index to the filler (cf. e.g. DE OS 24 11 760). The mechanical properties of the materials can also be improved by the addition of bis-BMA.

Through the matching of the refractive indices, a greater through-curing depth of the dental materials upon photopolymerization is achieved, but, because of the hydroxyl groups present, bis-GMA encourages the water absorption of the materials, which leads to a reduced durability under moist conditions. Moreover, bis-GMA frequently contains impurities, which are hard to remove, of bisphenol-A which has a pronounced oestrogenic action.

In addition to UDMA, the use of other di(meth)acrylate urethanes has been described. M. G. Buonocore and C. A. Casciani, New York State Dental Journal 35 (1969) 135, describe for example addition products of two moles of HEMA and one mole each of 2,4-toluylene diisocyanate, hydrogenated diphenylmethane diisocyanate, naphthalene diisocyanate or hexanemethylene diisocyanate. These are all crystalline compounds which can be processed to dental materials only together with liquid monomers.

U.S. Pat. No. 4,400,159 discloses urethane diacrylates which are obtained by reaction of aliphatic and aromatic diisocyanates with 3-methacrylol-2-hydroxypropyl esters. However, the substances tend to become discoloured, and the aromatic derivatives are crystalline compounds. These monomers are preferably combined with bis-GMA.

DE 195 44 671 A1 discloses urethane (meth)acrylates with cyclic carbonate groups which are said to show an increased speed of polymerization and a lower sensitivity to polymerization inhibition by oxygen.

U.S. Pat. No. 4,952,241, EP 0 254 185 B1, U.S. Pat. No. 4,904,750 and EP 0 658 582 A1 disclose prepolymeric (meth)acryl urethane derivatives which can be used above all as flexibilizing monomers or dilution monomers in combination with bis-GMA.

U.S. Pat. No. 4,386,912 relates to dental filling materials on the basis of tetrafunctional urethane acrylate monomers, which can be prepared by reaction of glycerol dimethacrylate with aromatic or aliphatic diisocyanates. Aliphatic diisocyanates are preferred as regards the coloration of the cured product.

B. Nabeth, J. F. Gerard, J. P. Pascault, J. Appl. Polym. Sci. 60 (1996) 2113, describe the synthesis of polyurethane (meth)-acrylates on the basis of polycaprolactone macrodiols using 1,3-bis (1-isocyanato-1-methylethyl)benzene (TMXDI). Low-molecular-weight urethane di(methacrylate) derivatives on the basis of TMXDI are not known at present.

The object of the invention is to prepare urethane di(meth)-acrylate derivatives capable of flowing and capable of polymerization, whose refractive index is compatible with that of customary dental filling materials, which do not to tend towards discolorations and which can replace bis-GMA in dental materials without impairing the mechanical properties of the materials.

This object is achieved by urethane di(meth)acrylate derivatives of 1,3-bis(1-isocyanato-1-methylethyl)benzene according to Formula (I),

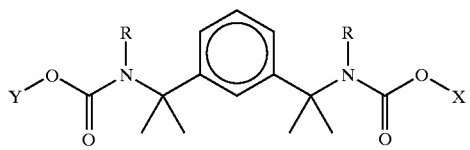

in which

R is hydrogen or a straight-chained $C_1$–$C_8$ alkyl radical, preferably hydrogen, methyl, ethyl, propyl, butyl or hexyl, quite particularly preferably hydrogen or methyl and X and Y independently of each other stand for

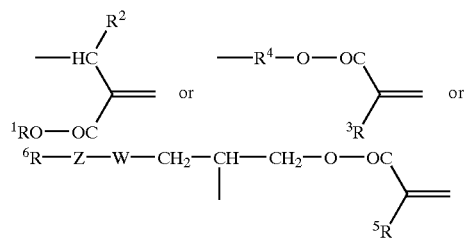

preferably

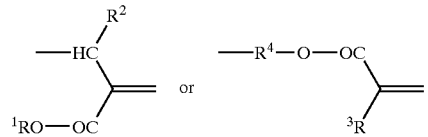

in which $R^1$ is a substituted or unsubstituted $C_6$- to $C_{12}$-aryl or $C_7$- to $C_{16}$-alkyl aryl or $C_7$- to $C_{12}$-aryl alkyl radical and $R^2$ is hydrogen, a $C_1$- to $C_5$-alkyl or a substituted or unsubstituted $C_6$- to $C_{12}$-aryl radical;

$R^3$ is hydrogen or a methyl radical and $R^4$ is a $C_1$- to $C_8$-alkylene radical which can be interrupted by oxygen atoms, or is a phenylene radical;

$R^5$ is hydrogen or a methyl radical, $R^6$ is a substituted or unsubstituted $C_6$- to $C_2$-aryl or $C_7$- to C16-alkyl aryl or $C_7$- to $C_{12}$-aryl alkyl radical, Z is —CO— or a chemical bond and W stands for oxygen, sulphur or NR [7], whereby $R^7$ is hydrogen or a straight-chained $C_1$- to $C_6$-alkyl radical.

R and $R^7$ preferably have the same meaning.

The aromatic groups both of the aryl and of the alkyl aryl radicals can be singly or repeatedly, preferably singly, substituted. Preferred substituents are halogen, in particular bromine, —$OCH_3$, —OH, —CN, —$CH_3$, —$C_2H_5$, —$NO_2$—COOH and —$COOCH_3$.

Preferred $C_7$- to $C_{12}$-aryl alkyl radicals are benzyl, a methyl-benzyl, α,α-dimethylbenzyl and α,α-diethylbenzyl, in particular benzyl.

Preferred definitions which can be chosen independently of one another are:

$R^1$ hydrogen or —$CH_3$, $R^2$ —$CH_3$, —$C_2H_5$, a benzyl or phenyl radical, $R^3$ hydrogen or a methyl radical, $R^4$ an ethylene, propylene, triethylene, butylene or phenylene radical, $R^5$ a methyl radical, $R^6$ a benzyl, phenyl or substituted phenyl radical, W oxygen, sulphur or NH, Z —CO— or a chemical bond and/or $R^7$ hydrogen.

Quite particularly preferred definitions which can be chosen independently of each other are:

$R^1$ hydrogen, $R^2$ hydrogen, a benzyl or phenyl radical, $R^3$ a methyl radical, $R^4$ an ethylene, triethylene or propylene radical, $R^5$ a methyl radical, $R^6$ a benzyl radical, W oxygen, Z —CO— and/or $R^7$ hydrogen.

Furthermore, urethane di(meth)acrylate derivatives in which X and Y have the same meaning are preferred.

Particularly preferred urethane di(meth)acrylate derivatives are:

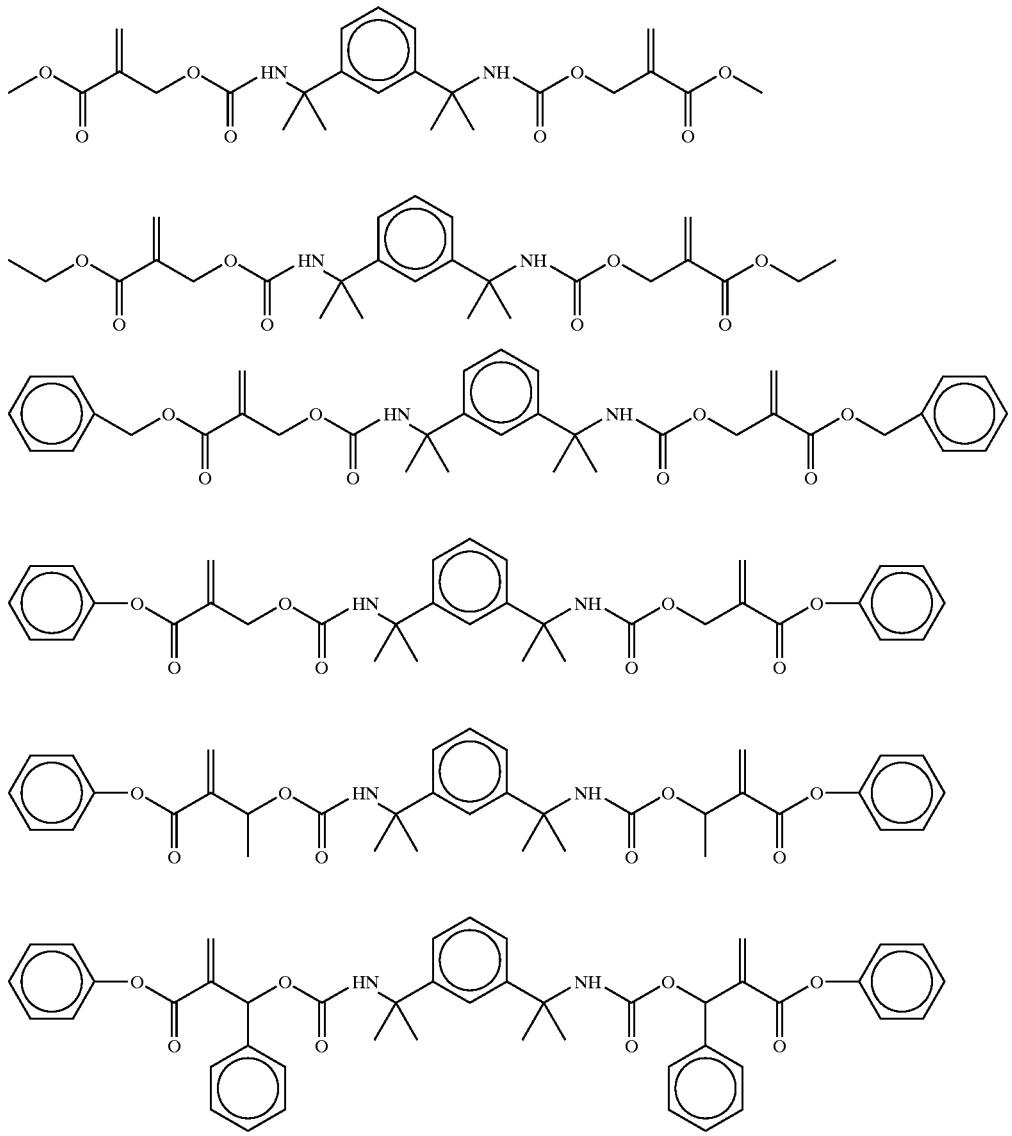

-continued
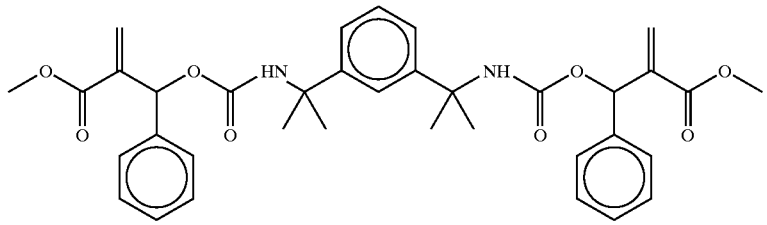
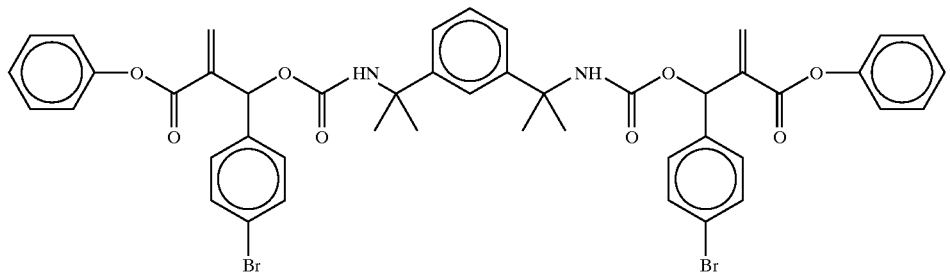
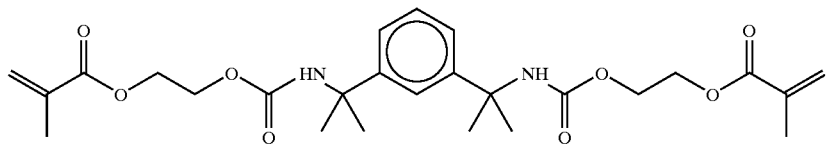
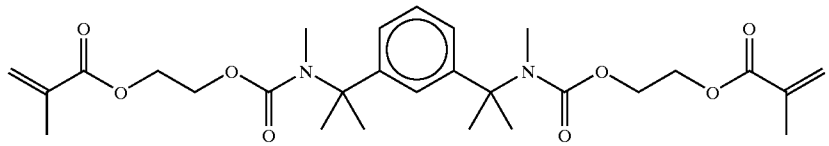
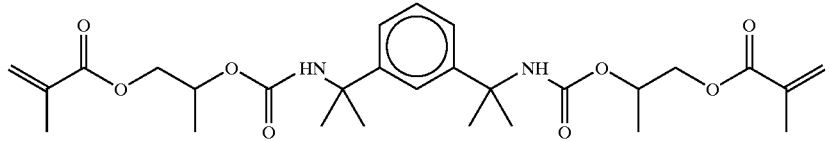
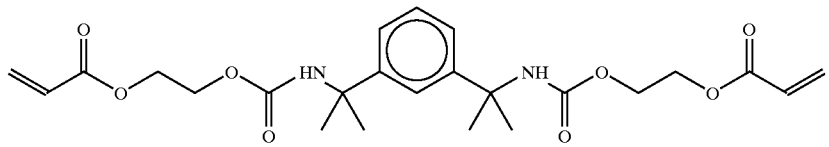
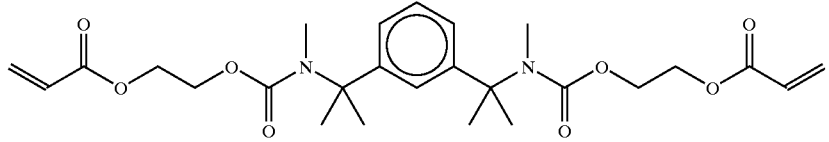
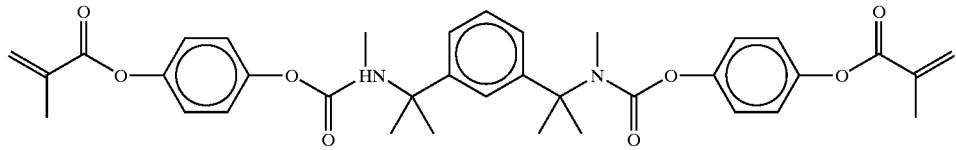
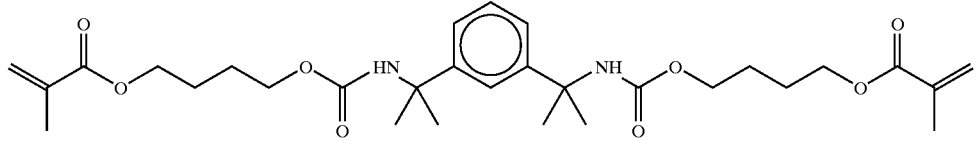

-continued
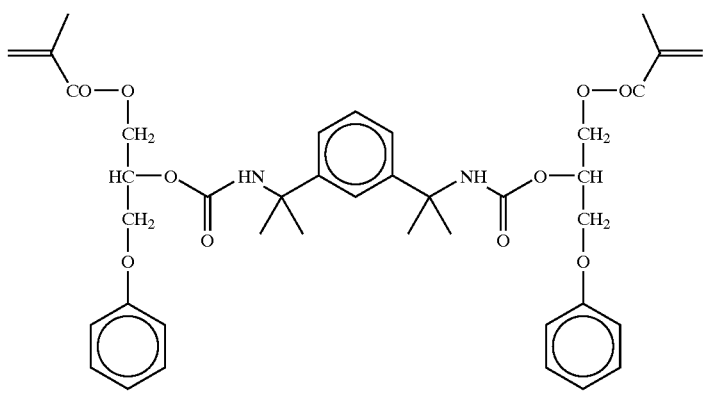
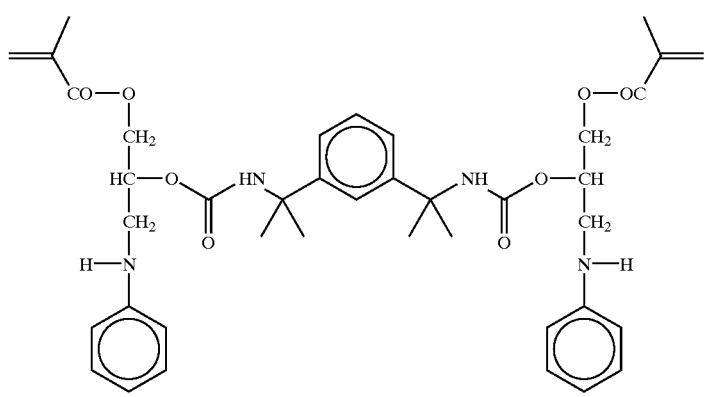
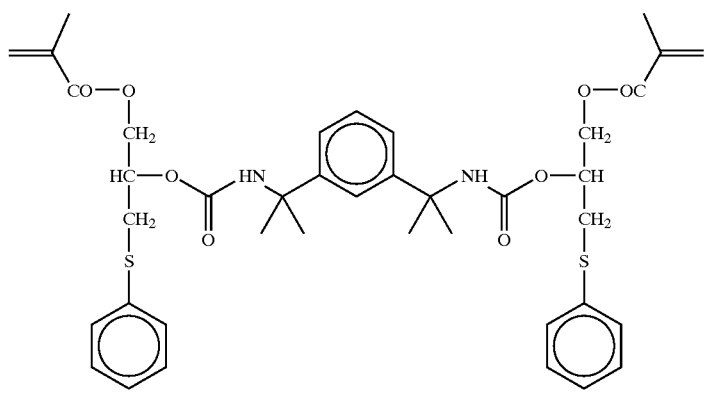
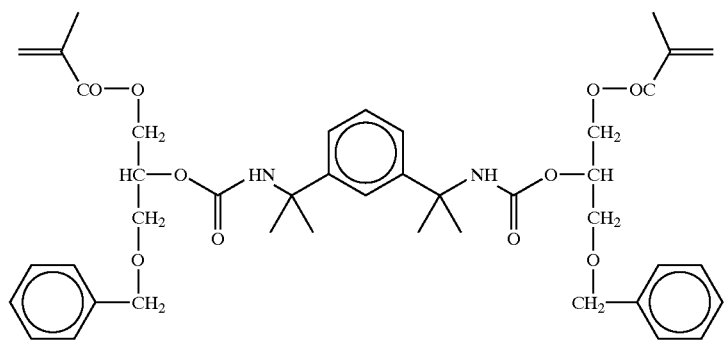

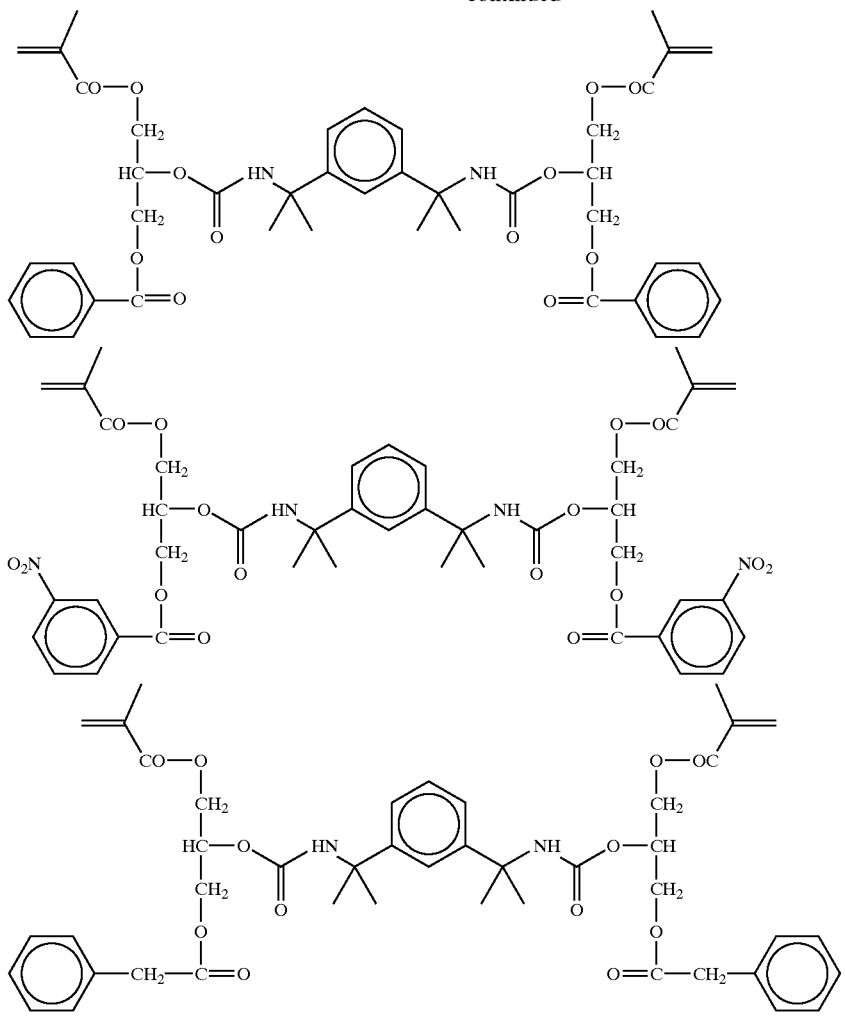

Furthermore, compounds according to Formula I in which R and $R^3$ independently of each other, are hydrogen or methyl and $R^4$ is ethylene or propylene are particularly preferred.

The urethane di(meth)acrylate derivatives according to the invention of formula (I) can be prepared by reaction of commercial 1,3-bis(1-isocyanato-1-methylethyl)benzene (TMXDI) with corresponding hydroxy(meth)acrylates X—OH or Y—OH and optionally subsequent alkylation of the formed adducts for example with a dialkyl sulphate.

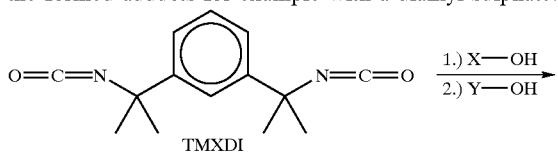

The preparation of the hydroxy(meth)acrylates X—OH and Y—OH can take place in a manner known per se (cf. e.g. C. Ferri, Reaktionen der organischen Synthese [*Organic Synthesis Reactions*], G. Thieme Verlag, Stuttgart 1978). The Baylis-Hillman reaction, catalysed by tertiary amines, of acrylates with aldehydes according to the reaction equation

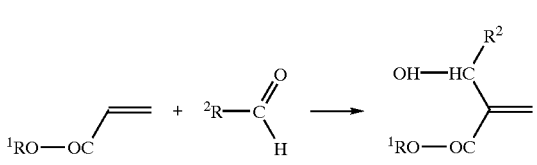

in which $R^1$ and $R^2$ have the meaning given above, is preferred. For example, 2-hydroxymethyl acrylic acid benzyl ester can be prepared by reaction of acrylic acid benzyl ester with formaldehyde:

Concrete Example

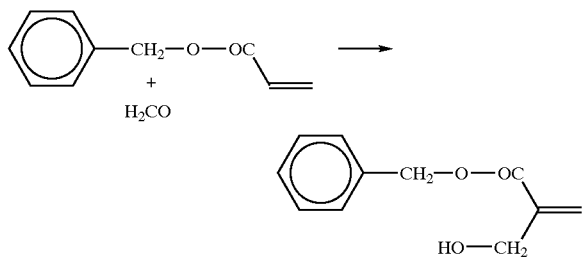

Further preferred is the unstoichiometric esterification of dihydroxy compounds with (meth)acrylic acid or (meth)acrylic acid chloride according to the reaction equation

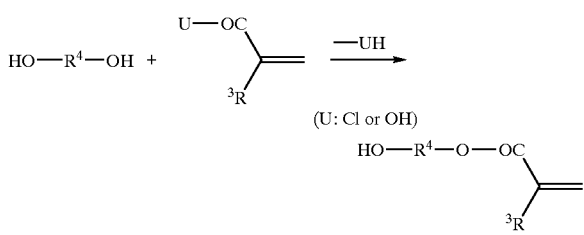

in which $R^3$ and $R^4$ have the meaning given above and U=Cl or is OH. For example, 4-hydroxyphenyl methacrylate is accessible by reaction of hydroquinone with methacrylic acid chloride:

Concrete Example

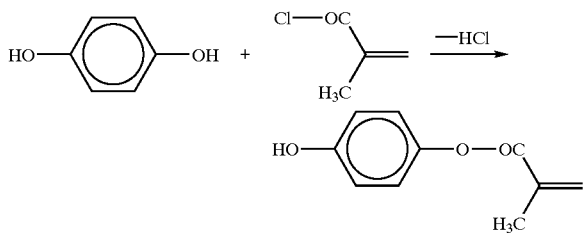

Moreover, the synthesis of suitable hydroxy(meth)acrylates can take place by reaction of glycidyl (meth)acrylate with O-nucleophilic reagents, such as alcohols, phenols or carboxylic acids according to the reaction equation

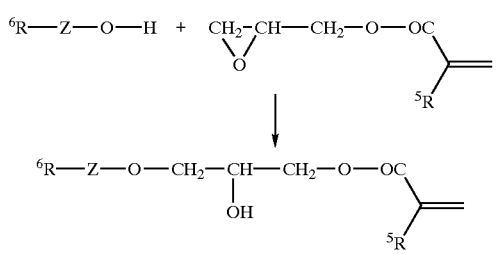

in which $R^5$ and $R^6$ have the meaning given above. For example, 1-benzylcarbonyloxy-2-hydroxypropyl methacrylate can be obtained by reaction of phenylacetic acid with glycidyl methacrylate:

Concrete Example

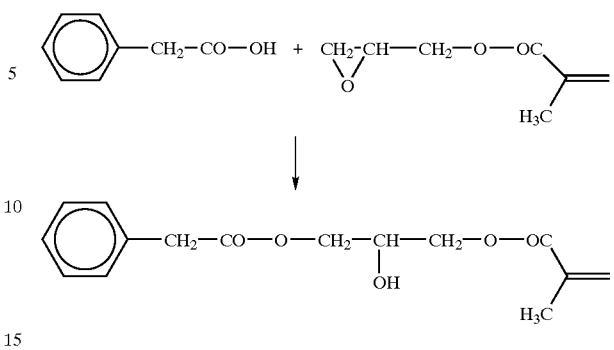

The urethane di(meth)acrylate derivatives according to the invention are suitable in particular for the production of polymers, adhesives and dental materials, such as filling composites, dental adhesives and fixing cements, with the urethane di(meth)acrylates acting as crosslinkers.

Derivatives with a refractive index of $n_D$=1.50 to 1.60, in particular 1.50 to 1.55, are preferred for the production of dental materials.

For the polymerization, the compounds according to the invention are mixed with initiators for radical polymerization and optionally additional radically polymerizable monomers and fillers plus other auxiliaries.

Suitable initiators are described for example in the Encyclopedia of Polymer Science and Technology, Vol. 13, Wiley-Intersci. Pub., New York etc. 1988, p. 754 et seq. Preferred initiators for cold polymerization are azo compounds such as azobis(isobutyronitrile) (AIBN) or azobis (4-cyanovaleric acid) or peroxides, such as dibenzoyl peroxide, dilauroyl peroxide, tert.-butyl peroctoate, tert.-butyl perbenzoate or di-(tert.-butyl) peroxide.

Benzpinacol and 2,2'-Di($C_1$–$C_8$-alkyl)benzpinacols in particular are suitable as initiators for hot curing.

Suitable photoinitiators for the UV or visible range are described by J. P. Foussier, J. F. Rabek (Pub.), Radiation Curing in Polymer Science and Technology, Vol. II, Elsevier Applied Science, London and New York 1993, pages 155 to 237. Preferred photoinitiators are benzoin ethers, dialkyl benzil ketals, dialkoxyacetophenones, acylphosphinic oxides, α-diketones, such as 10-phenanthrenequinone, diacetyl, furil, anisil, 4,4'-dichlorobenzil and 4,4'-dialkoxybenzil and camphor quinone.

Dibenzoyl peroxide, camphor quinone or acylphosphinic oxides are particularly suitable for the production of dental materials.

Difunctional crosslinker monomers are preferred as additional radically polymerizable monomers, with crosslinking bi- or higher-functional acrylates and methacrylates, such as for example UDMA, di- or triethylene glycol di(meth)acrylate (TEGDMA), decanediol di(meth)acrylate, trimethylol propane tri(meth)-acrylate, pentaerythritol tetra (meth)acrylate, butanediol (di)-methacrylate, 1,10-decanediol di(meth)acrylate diol di(meth)acrylate above all being suitable for producing adhesives or dental materials. These monomers are accessible by esterification of (meth)acrylic acid with suitable diols.

Organic as well as inorganic particles and fibres are suitable as fillers. Preferred inorganic fillers for producing dental materials are amorphous, spherical materials on the basis of mixed oxides from $SiO_2$, $ZrO_2$ and/or $TiO_2$ with an average particle size of 0.005 to 2.0 μm, preferably of 0.1 to 1 μm, as are disclosed for example in DE-PS 32 47 800, microfine fillers, such as pyrogenic silica or precipitated silica, as well as macro- or mini-fillers, such as quartz, glass ceramic or glass powder with an average particle size of 0.5 to 20 μm, as well as X-ray-opaque fillers, such as ytterbium trifluoride. The term mini-fillers is taken to mean fillers with a particle size of 0.5 to 1.5 μm, and the term macro-fillers to mean fillers with a particle size of 10 to 20 μm.

Glass, polyamide or carbon fibres can also be used as fillers. Suitable reinforcing fibres are described for example in the "Taschenbuch der Kunststoff-Additive", R. Gachter, H. Muller, Carl Hanser Verlag, Munich and Vienna 1990, pages 617 to 662.

The compositions according to the invention can also if needed contain other auxiliaries such as solvents, in particular water, ethyl acetate or ethanol, stabilizers, UV absorbers, dyestuffs, pigments and/or slip agents. The term stabilizers is taken to mean substances which prevent premature polymerization and thus above all increase the storage stability of monomer mixtures and composites without however impairing the properties of the cured materials. Preferred stabilizers are hydroquinone monomethyl-ether (MEHQ) and 2,6-di-tert.-butyl-4 methylphenol (BHT).

Dental materials preferably have the following composition:
1 to 99 wt.-%, preferably 10 to 80 wt.-% and particularly preferably 20 to 70 wt.-% of one or more urethane di(meth)acrylates,
0 to 80 wt.-%, preferably 0 to 60 wt.-% and particularly preferably 0 to 50 wt.-% of one or more other radically polymerizable monomers,
0 to 90 wt.-% fillers and
0.01 to 5 wt.-%, preferably 0.01 to 2 wt.-% of an initiator for radical polymerization.

The filler content is crucially determined by the intended use and is preferably 0 to 20 wt.-% in the case of adhesives, preferably 20 to 60 wt.-% in the case of cements and 50 to 85 wt.-% in the case of filling composites.

The proportion of the other auxiliaries usually lies in the range from 100 ppm to 1.0 wt.-% in each case, and in the case of dyestuffs and pigments, depending on colouring capacity, also in the range from 10 ppm up to 1.0 wt.-%.

The dental materials according to the invention preferably contain no bis-GMA, but have mechanical properties which correspond in every respect to those of materials containing bis GMA. Under moist conditions, the materials according to the invention display clearly better mechanical properties than the materials containing bis-GMA.

The urethane di(meth)acrylate derivatives according to the invention are moreover also suitable for the production of other medical or technical, radically curing adhesives, cements and composites, such as for example surgical bone cements, contact lenses, adhesives for optical parts, UV-curable lacquers, coatings and covering materials and also matrix resins for composite materials.

The invention is explained in more detail in the following with reference to embodiments.

Example 1

Synthesis of TMXUDEMA 1,3-bis-(2-aza-1,1,9-trimethyl-3,8-dioxo-4,7-dioxa-9-decen-1-yl)-benzene

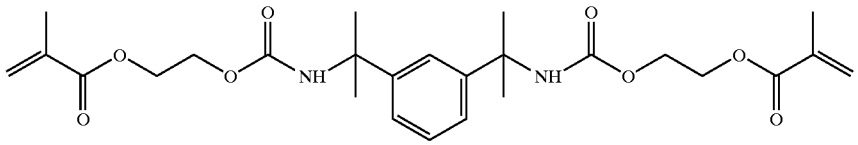

TMXUDEMA 90.7 g (371 mmol) of TMXDI were added dropwise within 30 minutes to 101.1 g (742 mmol) of HEMA and 0.19 g of dibutyltin dilaurate (Metatin 812, Acima). After 36 hours' stirring at 70° C the iso-cyanate had completely reacted off (reaction monitoring by means of IR spectroscopy). 300 ml of methylene chloride were added and the reaction mixture washed twice with 200 ml of NaOH each time and three times with 100 ml of water each time. The methylene chloride phase was dried with sodium sulphate and the solvent evaporated off, after the addition of 80 mg of hydro-quinone monomethyl ether (MEHQ), at the rotation evaporator at ca. 250 mbar. 169 g (88% yield) of a colourless, highly viscous liquid ($n_D^{25}$=1.5120) with a shearing viscosity (23° C.) of 860 Pass were obtained.

IR (film):3361 (s), 2976 (s), 1714 (s), 1637 (m), 1504 (s), 1384 (s), 1174 (s), 1043 (m) and 944 (m) cm$^{-1}$.

$^1$H-NMR (400 MHz, CDCl$_3$): 7.43 and 7.27 (m, 4H, aromatic); 6.13 and 5.77 (2 s, 4 H, =CH$_2$); 5.29 (br, 2 H, NH); 4.24–4.40 (br, 8 H, OCH$_2$CH$_2$O); 1.95 (s, 6H=C—CH$_3$) and 1.66 (s, 12 H, CH$_3$) ppm.

Example 2

Synthesis of TMXUDPMA 1,3-bis-(2-aza-1,1,5,9-tetramethyl-3,8-dioxo-4,7-dioxa-9-decen-1-yl)-benzene

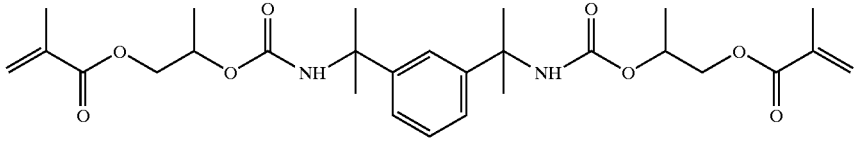

TMXUDPMA 55.0 g (225 mmol) of TMXDI were added dropwise within 10 minutes to 68.3 g (450 mmol) of 95% hydroxypropyl methacrylate and 0.1 g of Metatin 812. After 3 days' stirring at 60° C. the isocyanate had completely reacted off (reaction monitoring by means of IR spectroscopy). The reaction mixture was reacted with 200 ml of methylene chloride and washed twice with 100 ml of NaOH each time and three times with 100 ml of water each time. The methylene chloride phase was dried with sodium sulphate and the solvent evaporated off, after the addition of 80 mg of MEHQ, at the rotation evaporator at ca. 250 mbar. 106 g (88% yield) of a colourless, highly viscous liquid ($n_D^{25}$= 1.5018) with a shearing viscosity (23° C.) of 1665 Pa·s were obtained.

IR (film): 3366 (m), 2980 (s), 1719 (s), 1637 (m), 1521 (s), 1458 (s), 1296 (m), 1248 (s), 1172 (s) and 1088 (m) cm$^{-1}$.

$^1$H-NMR (400 MHz, CDCl$_3$): 10.86 (br, 2 H, NH); 7.26 and 7.22 (m, 4H, aromatic); 6.22 and 5.69 (2 s, 4 H, =CH$_2$); 5.00 (m, *, OCH); 4.09–4.29 (m, *, OCH$_2$); 1.93 (s, 6 H =C—CH$_3$); 1.62 (s, 12 H, CH$_3$) and 1.32 (d, *, CHC$\underline{H}_3$) ppm (with Σ*0 12 H).

Example 3

Composites on the Basis of TMXUDEMA and TMXUDPMA

Three composite pastes K-1 to K-3 with the compositions shown in Table I (all figures in wt.-%) were prepared in a planetary kneader (type LPM 2SP, Linde) and deaerated at 200 mbar for ten minutes.

Composition K-3 contains bis-GMA instead of the urethane di(meth)acrylate derivatives according to the invention and serves as a comparative example.

To determine the mechanical properties, testpieces (2 mm×2 mm×20 mm) were formed from the pastes and cured by 6 minutes' exposure to light with a dental radiation source (Spektramat, Vivadent, λ=400 to 500 nm). The polymerization shrinkage (ΔV) was calculated from the difference between the paste and composite densities determined by gas pyknometry, and the bending strength (BS), the bending E-modulus (BEM) were determined according to ISO standard 4049 (1988). For this, the testpieces were stored dry at 37° C. for 24 hours or for 24 hours or 7 days in water (WS) or boiled for 24 hours in deionized water (B). The results of the studies are listed in Table II.

TABLE I

| Composition of the composite pastes (wt.-%) | | | |
|---|---|---|---|
| Component | K-1 | K-2 | K-3[a)] |
| TMXUDEMA | 7.59 | — | — |
| TMXUDPMA | — | 7.59 | — |
| bis-GMA | — | — | 7.59 |
| UDMA | 6.72 | 6.72 | 6.72 |
| TEGDMA | 3.64 | 3.64 | 3.64 |
| Ytterbium fluoride (Rhone-Poulenc) | 14.89 | 14.89 | 14.89 |
| Barium glass[b)] | 51.61 | 51.61 | 51.61 |
| Sphärosil ®[c)] | 14.39 | 14.39 | 14.39 |
| AEROSIL ® OX-50[d)] | 1.00 | 1.00 | 1.00 |
| Hydroquinone methyl ether | 0.02 | 0.02 | 0.02 |

TABLE I-continued

| Composition of the composite pastes (wt.-%) | | | |
|---|---|---|---|
| Component | K-1 | K-2 | K-3[a)] |
| Camphor quinone | 0.05 | 0.05 | 0.05 |
| N-(2-cyanoethyl-N-methyl-aniline | 0.09 | 0.09 | 0.09 |

[a)]comparative example
[b)]silanized barium aluminium silicate glass powder (Schott), proportion with a grain size <7 μm: 99%
[c)]SiO$_2$—ZrO$_2$ mixed oxide (Tokoyama Soda), secondary grain size <7 μm
[d)]silanized pyrolysis silica (Degussa)

TABLE II

| Mechanical properties of the cured composite materials | | | |
|---|---|---|---|
| Property | K-1 | K-2 | K-3[a)] |
| ΔV (vol.-%) | −2.9 | −2.8 | −2.8 |
| BS, dry (MPa) | 141 | 120 | 116 |
| BS, 24 h WS (MPa) | 153 | 145 | 140 |
| BS, 7 d WS (MPa) | 147 | 144 | 121 |
| BS, 24 h B (MPa) | 143 | 129 | 123 |
| BEM, dry (GPa) | 13.14 | 13.62 | 12.13 |
| BEM, 24 h WS/GPa | 12.40 | 12.56 | 11.44 |
| BEM, 7 d WS (GPa) | 12.58 | 11.66 | 11.63 |
| BEM, 24 h B (GPa) | 12.92 | 11.52 | 10.56 |

[a)]Comparative example

What is claimed is:
1. A dental composition consisting of:
1 to 99 wt.-% of one or more urethane di(meth)acrylate derivatives of 1,3-bis(1-iso-cyanato-1-methylethyl) benzene according to Formula (I),

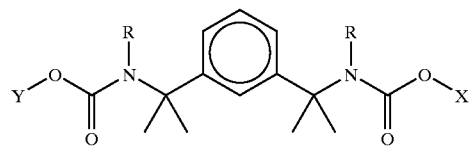

in which
R is hydrogen or a straight-chained Cl-Cs alkyl radical,
X and Y independently of each other stand for

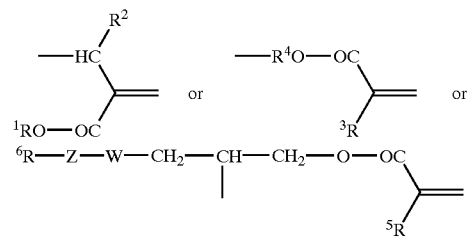

in which
R$^1$ is hydrogen or substituted or unsubstituted C$_6$- to C$_{12}$-aryl, C$_7$- to C$_{16}$-alkyl aryl or C$_7$- to C$_{12}$-aryl alkyl radical,
R$^2$ is hydrogen, a C$_1$- to C$_5$-alkyl or a substituted or unsubstituted C$_6$- to C$_{12}$-aryl radical,
R$^3$ is hydrogen or a methyl radical,
R$^4$ is a C$_1$- to C$_8$-alkylene radical which can be interrupted by oxygen atoms, or a phenylene radical,
R$^5$ is hydrogen or a methyl radical,
R$^6$ is a substituted or unsubstituted C$_6$- to C$_{12}$-aryl, C$_7$- to C$_{16}$-alkyl aryl or C$_7$- to C$_{12}$-aryl alkyl radical, Z is —CO— or a chemical bond and
W stands for oxygen, sulphur or $NR^7$, whereby
$R^7$ is hydrogen or a straight-chained $C_1$- to $C_6$-alkyl radical;
0 to 80 wt.-% of one or more radically difunctional crosslinker monomers;
0 to 90 wt.-% fillers;
0.01 to 5 wt.-% of an initiator for the radical polymerization; and
0 to 1 wt.-% of auxiliaries selected from the group consisting of solvents, stabilizers, UV absorbers, dyestuffs, pigments and slip agents.

2. A dental composition according to claim 1, wherein the composition contains
20 to 70% of one or more of the urethane di(meth)acrylate derivatives;
0 to 80% of one or more radically difunctional crosslinker monomers;
0 to 85% fillers; and/or
0.01 to 2% of an initiator for the radical polymerization plus optional auxiliaries selected from the group consisting of solvents, stabilizers, UV absorbers, dyestuffs, pigments and slip agents where necessary.

3. A dental composition according to claim 1, wherein X and Y independently of each other stand for

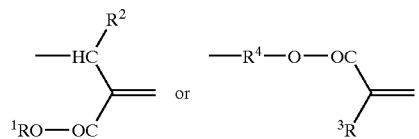

4. A dental composition according to claim 1, wherein the aryl groups are singly or repeatedly substituted by halogen, —$OCH_3$, —OH, —CN, —$CH_3$, —$C_2H_5$, —$NO_2$, —COOH and/or —$COOCH_3$.

5. A dental composition according to claim 1, wherein X and Y are the same.

6. A dental composition according to claim 1, wherein
R is hydrogen, methyl, ethyl, propyl, butyl or hexyl, is hydrogen or —$CH_3$,
$R^1$ is —$CH_3$, —$C_2H_5$, a benzyl, or phenyl radical,
$R^3$ is hydrogen or a methyl radical,
$R^4$ is an ethylene, propylene, triethylene, butylene, or phenylene radical,
$R^5$ is a methyl radical,
$R^6$ is a benzyl, phenyl, or substituted phenyl radical,
W is oxygen, sulphur, or NH,
Z is —CO— or a chemical bond and/or
$R^7$ is hydrogen.

7. A dental composition according to claim 6, wherein
$R^1$ is hydrogen,
$R^2$ is hydrogen, a benzyl, or phenyl radical,
$R^3$ is a methyl radical,
$R^4$ is an ethylene, propylene, or triethylene radical,
$R^5$ is a methyl radical,
$R^6$ is a benzyl radical,
W is oxygen,
Z is —CO— and/or
$R^7$ is hydrogen.

8. A process for the production of a urethane di(meth) acrylate derivative according to claim 1, wherein 1,3-bis(1-isocyanato-1-methylethyl)benzene is reacted with hydroxy (meth)acrylates according to the formulae X—OH or Y—OH, X and Y having the given meaning, and the reaction product is optionally then alkylated.

9. A dental composition according to claim 1, wherein it contains, as filler, amorphous spherical materials on the basis of mixed oxides from $SiO_2$, $ZrO_2$, $TiO_2$, or combinations thereof, pyrogenic silica, precipitation silica, quartz, glass ceramic, glass powder, ytterbium fluoride, or combinations thereof.

10. A dental composition according to claim 1, wherein it contains, as initiator, azobis(isobutyro-nitrile), azobis(4-cyanovaleric acid), dibenzoyl peroxide, dilauroyl peroxide, tert.-butyl peroctoate, tert.-butyl perbenzoate, di-(tert.-butyl)-peroxide, benzpinacol, a 2,2'-di($C_1$–$C_8$-alkyl) benzpinacol, a benzoin ether, a dialkyl benzil ketal, dialkoxyacetophenone, acyiphosphinic oxide, 9,10-phenanthrenequinone, diacetyl, furil, anisil, 4,4'-dichlorobenzil, 4,4'-dialkoxybenzile, camphor quinone, or combinations thereof.

11. A radically curable adhesive or cement produced from the dental composition according to claim 1.

12. A radically curable composite produced from the dental composition according to claim 1.

13. A product formed from the dental composition according to claim 1, wherein the product is selected from the group consisting of surgical bone cements, contact lenses, adhesives for optical parts, UV-curable lacquers, coatings, covering materials, matrix resins, and composite materials.

14. The dental composition of claim 1, wherein when R is hydrogen and $R^4$ is dimethylene, $R^3$ is not methyl.

15. A dental composition according to claim 1, wherein said one or more urethane di(meth)acrylate derivatives have a refractive index of from 1.50 to 1.60.

16. A dental composition according to claim 1, wherein one or more urethane di(meth)acrylate derivatives of 1,3-bis(1-iso-cyanato-1-methylethyl)benzene is:

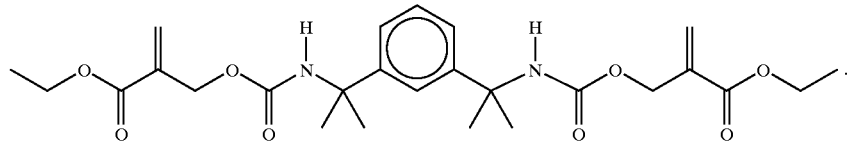

17. A dental composition according to claim 1, wherein one or more urethane di(meth)acrylate derivatives of 1,3-bis(1-iso-cyanato-1-methylethyl)benzene is:

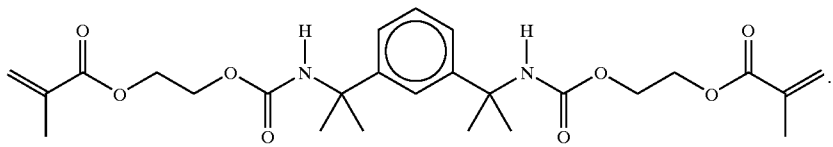

18. A dental composition according to claim 1, wherein one or more urethane di(meth)acrylate derivatives of 1,3-bis(1-iso-cyanato-1-methylethyl)benzene is:

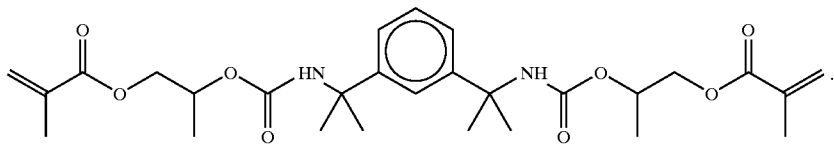

19. A dental composition according to claim 1, wherein one or more urethane di(meth)acrylate derivatives of 1,3-bis(1-iso-cyanato-1-methylethyl)benzene is:

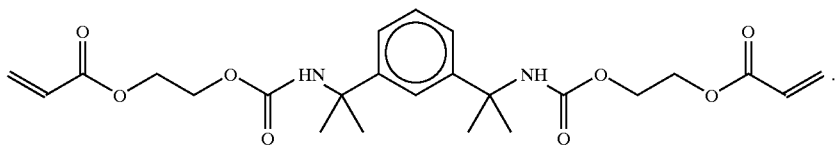

20. A dental composition consisting of:
1 to 99 wt.-% of one or more urethane di(meth)acrylate derivatives of 1,3-bis(1-iso-cyanato-1-methylethyl) benzene according to Formula (I),

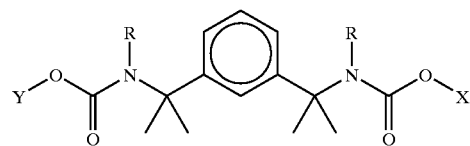

in which
R is hydrogen or a straight-chained $C_1$–$C_8$ alkyl radical,
X and Y independently of each other stand for

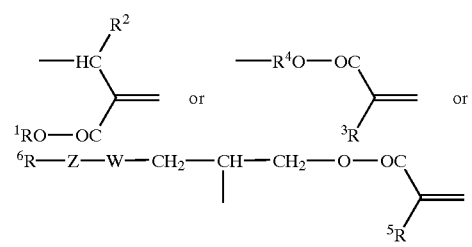

in which
$R^1$ is hydrogen or substituted or unsubstituted $C_6$- to $C_{12}$-aryl, $C_7$- to $C_{16}$-alkyl aryl or $C_7$- to $C_{12}$-aryl alkyl radical,
$R^2$ is hydrogen, a $C_1$- to $C_5$-alkyl or a substituted or unsubstituted $C_6$- to $C_{12}$-aryl radical,
$R^3$ is hydrogen or a methyl radical,
$R^4$ is a $C_1$- to $C_8$-alkylene radical which can be interrupted by oxygen atoms, or a phenylene radical,
$R^5$ is hydrogen or a methyl radical,
$R^6$ is a substituted or unsubstituted $C_6$- to $C_{12}$-aryl, $C_7$- to $C_{16}$-alkyl aryl or $C_7$- to $C_{12}$-aryl alkyl radical,
Z is —CO— or a chemical bond and
W stands for oxygen, sulphur or $NR^7$, whereby
$R^7$ is hydrogen or a straight-chained $C_1$- to $C_6$-alkyl radical;
0 to 80 wt.-% of one or more radically polymerizable monomers selected from the group consisting of 7,7,9-trimethyl-4-13-dioxo-3,14-dioxa-5,12-diaza-hexadecan-1,16-diyldimethacrylate, di- or triethylene glycol di(meth)acrylate (TEGDMA), decanediol di(meth)acrylate, trimethylol propane tri(meth) acrylate, pentaerythritol tetra(meth)acrylate, 1,10-decanediol di(meth)acrylate, 1,12-dodecanediol di(meth)acrylate and butanediol(di)methacrylate;
0 to 90 wt.-% fillers;
0.01 to 5 wt.-% of an initiator for radical polymerization; and
0 to 1 wt.-% of auxiliaries selected from the group consisting of solvents, stabilizers, UV absorbers, dyestuffs, pigments and slip agents.

21. A dental composition according to claim 20, wherein X and Y independently of each other stand for

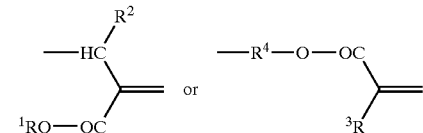

22. A dental composition according to claim 20, wherein the aryl groups are singly or repeatedly substituted by halogen, —$OCH_3$, —OH, —CN, —$CH_3$, —$C_2H_5$, —$NO_2$, —COOH and/or —$COOCH_3$.

23. A dental composition according to claim 20, wherein X and Y are the same.

24. A dental composition according to claim 20, wherein
R is hydrogen, methyl, ethyl, propyl, butyl or hexyl,
$R^1$ is hydrogen or —$CH_3$,
$R^2$ is —$CH_3$, —$C_2H_5$, a benzyl, or phenyl radical,
$R^3$ is hydrogen or a methyl radical,
$R^4$ is an ethylene, propylene, triethylene, butylene, or phenylene radical,
$R^5$ is a methyl radical,
$R^6$ is a benzyl, phenyl, or substituted phenyl radical,
W is oxygen, sulphur, or NH,
Z is —CO— or a chemical bond and/or
$R^7$ is hydrogen.

25. A dental composition according to claim 24, wherein
$R^1$ is hydrogen,
$R^2$ is hydrogen, a benzyl, or phenyl radical,
$R^3$ is a methyl radical,
$R^4$ is an ethylene, propylene, or triethylene radical,
$R^5$ is a methyl radical,
$R^6$ is a benzyl radical,
W is oxygen,
Z is —CO— and/or
$R^7$ is hydrogen.

26. A process for the production of a urethane di(meth)acrylate derivative according to claim 24, wherein 1,3-bis(1-isocyanato-1-methylethyl)benzene is reacted with hydroxy(meth)acrylates according to the formulae X—OH or Y—OH, X and Y having the given meaning, and the reaction product is optionally then alkylated.

27. A dental composition according to claim 20, wherein the composition contains 20 to 70% of one or more of the urethane di(meth)acrylate derivatives;

0 to 80% of one or more radically polymerizable monomers;

0 to 85% fillers; and/or 0.01 to 2% of an initiator for the radical polymerization plus optional auxiliaries selected from the group consisting of solvents, stabilizers, UV absorbers, dyestuffs, pigments and slip agents where necessary.

28. A dental composition according to claim 20, wherein it contains, as filler, amorphous spherical materials on the basis of mixed oxides from $SiO_2$, $ZrO_2$, $TiO_2$, or combinations thereof, pyrogenic silica, precipitation silica, quartz, glass ceramic, glass powder, ytterbium fluoride, or combinations thereof.

29. A dental composition according to claim 20, wherein it contains, as initiator, azobis(isobutyro-nitrile), azobis(4-cyanovaleric acid), dibenzoyl peroxide, dilauroyl peroxide, tert.-butyl peroctoate, tert.-butyl perbenzoate, di-(tert.-butyl)-peroxide, benzpinacol, a 2,2'-di($C_1$–$C_8$-alkyl) benzpinacol, a benzoin ether, a dialkyl benzil ketal, dialkoxyacetophenone, acylphosphinic oxide, 9,10-phenanthrenequinone, diacetyl, furil, anisil, 4,4'-dichlorobenzil, 4,4'-dialkoxybenzile, camphor quinone, or combinations thereof.

30. A radically curable adhesive or cement produced from the dental composition according to claim 20.

31. A radically curable composite produced from the dental composition according to claim 20.

32. A product formed from the dental composition according to claim 20, wherein the product is selected from the group consisting of surgical bone cements, contact lenses, adhesives for optical parts, UV-curable lacquers, coatings, covering materials, matrix resins, and composite materials.

33. The dental composition of claim 20, wherein when R is hydrogen and $R^4$ is dimethylene, $R^3$ is not methyl.

34. A dental composition according to claim 20, wherein said one or more urethane di(meth)acrylate derivatives have a refractive index of from 1.50 to 1.60.

* * * * *